United States Patent [19]

Sauter et al.

[11] Patent Number: 5,081,142
[45] Date of Patent: Jan. 14, 1992

[54] DERIVATIVES OF 1-HYDROXY-1,2,4-TRIAZOLE AND FUNGICIDES AND GROWTH REGULATORS CONTAINING THEM

[75] Inventors: Hubert Sauter, Mannheim; Thomas Zierke, Boehl-Iggelheim; Wolfgang Reuther, Heidelberg; Ulf Baus, Dossenheim; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 589,216

[22] Filed: Sep. 28, 1990

[30] Foreign Application Priority Data

Sep. 30, 1989 [DE] Fed. Rep. of Germany ....... 3932752

[51] Int. Cl.$^5$ ............ A01N 43/80; A01N 43/74; A01N 43/653; A01N 43/54
[52] U.S. Cl. ............... 514/384; 514/184; 514/256; 514/269; 514/270; 514/272; 514/274; 514/275; 514/333; 514/340; 514/341; 514/342; 514/343; 514/365; 514/369; 514/370; 514/378; 514/380; 544/4; 544/300; 544/310; 544/316; 544/317; 544/319; 544/320; 544/321
[58] Field of Search ............ 544/316, 399, 331, 300, 544/310, 321, 324; 546/256, 276, 278, 279; 548/243, 247, 244, 262.2, 266.6, 101, 182, 183, 184, 193, 197, 245, 246, 266.6, 267.8, 101, 268.6; 514/333, 340, 378, 380, 269, 256, 270, 272, 274, 275, 370

[56] References Cited

U.S. PATENT DOCUMENTS 4,987,143  1/1991  Baus et al. .......... 548/262.2
4,988,721  1/1991  Baus et al. .......... 548/262.2

FOREIGN PATENT DOCUMENTS 165777  12/1986  European Pat. Off.

Primary Examiner—Patricia L. Morris
Attorney, Agent, or Firm—Oblon, Spivak, McClelland, Maier & Neustadt

[57] ABSTRACT

Compounds of the formula I

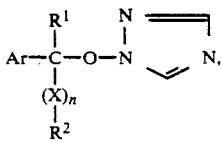

where
Ar is unsubstituted or substituted phenyl, pyridyl, thienyl or napthyl,
$R^1$ is hydrogen or CN,
$R^2$ is unsubstituted or substituted aryl, hetaryl, alkyl or cycloalkyl, or is unsubstituted or substituted alkenyl or alkynyl,
x is $CH_2$, O or S and
n is 0 or 1, their plant-tolerated acid addition salts and metal complexes, and fungicides and growth regulators containing these compounds.

5 Claims, No Drawings

DERIVATIVES OF 1-HYDROXY-1,2,4-TRIAZOLE AND FUNGICIDES AND GROWTH REGULATORS CONTAINING THEM

The present invention relates to novel derivatives of 1-hydroxy-1,2,4-triazole, their preparation, their use as fungicides and plant growth regulators, fungicides and plant growth regulators which contain the novel active ingredients and methods for controlling fungi and for regulating plant growth using these active ingredients.

EP 165777 discloses azole derivatives, e.g. 1-bis-(4-fluorophenyl)-methyl-1H-1,2,4-triazole, of the formula

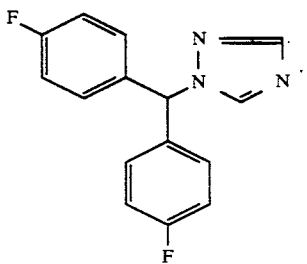

which act as aromatase inhibitors. However, their fungicidal action is not sufficient.

We have found novel compounds of the formula I

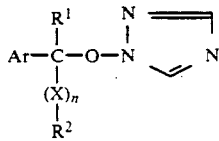

where

Ar is phenyl which is unsubstituted or monosubstituted or polysubstituted by halogen, $C_1$–$C_4$-alkoxy, $C_1$–$C_4$-alkyl, trifluoromethyl, $C_1$–$C_4$-alkoximino or unsubstituted or halogen- or trifluoromethyl-substituted phenyl or phenoxy, or is pyridyl which is unsubstituted or substituted by the same radicals, thienyl which is unsubstituted or substituted by the same radicals or naphthyl which is unsubstituted or substituted by the same radicals, $R^1$ is hydrogen or, where n is 0, is additionally CN, $R^2$ is aryl which is unsubstituted or monosubstituted or polysubstituted by halogen, $C_1$–$C_4$-alkyl, $C_1$–$C_4$-alkoximino, $C_1$–$C_4$-alkoxy or trifluoromethyl, or is hetaryl which is unsubstituted or substituted by the same radicals, or is unsubstituted or $C_1$–$C_4$-alkyl-substituted $C_3$–$C_8$-cycloalkyl or is straight-chain or branched $C_1$–$C_6$-alkyl which is unsubstituted or monosubstituted or polysubstituted by halogen, $C_3$–$C_6$-cycloalkyl, aryl or aryloxy, or is $C_2$–$C_6$-alkenyl, which is unsubstituted or substituted by the same radicals or is $C_2$–$C_6$-alkynyl which is unsubstituted or substituted by the same radicals, X is $CH_2$, O or S and n is 0 or 1, and their plant-tolerated acid addition salts and metal complexes, which have a very high fungitoxic action coupled with excellent toleration by plants. They also have powerful growth-regulating actions in combination with very good toleration by plants, even at low application rates.

The novel compounds of the formula I generally contain centers of chirality. They are generally obtained as racemates or may be obtained as diastereomer mixtures. In the case of some of the novel compounds, pure diastereomeric compounds can be isolated by distillation or column chromatography or on the basis of solubility differences. Pure enantiomeric compounds can be obtained, for example, by resolution of racemates using a chiral reagent by known methods, for example via diastereomeric salts. Regarding the use of the novel compounds as fungicides and growth regulators, both the diastereomers or the enantiomers and the stereoisomer mixtures obtained in the synthesis are suitable. The present invention relates to all of these.

Ar is, for example, phenyl, halophenyl, 4-fluorophenyl, 4-chlorophenyl, 4-bromophenyl, 4-trifluoromethylphenyl, $C_1$–$C_4$-alkylphenyl, 4-methylphenyl, 4-tert-butylphenyl, $C_1$–$C_4$-alkoxyphenyl, 4-methoxyphenyl, $C_1$–$C_4$-alkoximinophenyl, 4-methoximinophenyl, 2,4-dichlorophenyl, 3,4-dichlorophenyl, 2,6-dichlorophenyl, 3-trifluoromethylphenyl, 3-fluorophenyl, 2-fluorophenyl, 2-chlorophenyl, 2-bromophenyl, 2-methylphenyl, 4-fluoro-2-chlorophenyl, 4-chloro-2-fluorophenyl, 4-ethoximinophenyl, 2-methoxyphenyl, 2-pyridyl, 3-pyridyl, 4-pyridyl, 1-naphthyl, 2-naphthyl, 2-thienyl, 3-thienyl, 4-n-butoxyphenyl, 3,5-dimethoxyphenyl, 2-methoxy-4-methylphenyl, 3-chlorophenyl, 3,5-dichlorophenyl or 2-methyl-4-chlorophenyl.

$R^2$ is, for example, $C_1$–$C_6$-alkyl, in particular $C_1$–$C_4$-alkyl, methyl, ethyl, n-propyl, isopropyl, n-butyl, isobutyl, but-2-yl, tert-butyl, pentyl, pent-2-yl, neopentyl, hexyl, hex-2-yl, benzyl, halobenzyl, 4-chlorobenzyl, 2-chlorobenzyl, 4-fluorobenzyl, 2,4-dichlorobenzyl, 2-fluorobenzyl, $C_1$–$C_4$-alkylbenzyl, 2-methylbenzyl, 2-phenylethyl, 2-(4-chlorophenyl)-ethyl, 2-(4-fluorophenyl)-ethyl, 2-(2-methylphenyl)-ethyl, 2-(2,4-dichlorophenyl)-ethyl, 2-(4-methylphenyl)-ethyl, 2-(2-chlorophenyl)-ethyl, 2-(2-chloro-4-fluorophenyl)-ethyl, 2-(4-tert-butylphenyl)-ethyl, $C_3$–$C_8$-cycloalkyl, cyclopropyl, 1-methylcyclopropyl, cyclobutyl, cyclopentyl, cyclohexyl, 4-methylcyclohexyl, cycloheptyl, cyclooctyl, phenyl, halophenyl, 4-fluorophenyl, 4-chlorophenyl, 4-bromophenyl, 4-trifluoromethylphenyl, $C_1$–$C_4$-alkoxyphenyl, 4-methoximinophenyl, 2,4-dichlorophenyl, 3,4-dichlorophenyl, 2,6-dichlorophenyl, 3-trifluoromethylphenyl, 3-fluorophenyl, 2-fluorophenyl, 2-chlorophenyl, 3-chlorophenyl, 3,5-dichlorophenyl, 2-methyl-4-chlorophenyl, 4-n-butoxyphenyl, 3,5-dimethoxyphenyl, 2-methoxy-4-methylphenyl, 2-bromophenyl, 2-methylphenyl, 4-fluoro-2-chlorophenyl, 4-chloro-2-fluorophenyl, 4-ethoximinophenyl, 2-methoxyphenyl, phenoxyethyl, 2-fluorophenoxyethyl, 4-fluorophenoxybutyl, 4-fluorophenoxypropyl, 4-chlorophenoxyethyl, 2-fluorophenoxybutyl, 2-fluorophenoxyethyl, 2,4-dichlorophenoxyethyl, 4-fluorophenoxymethyl, 4-chlorophenoxymethyl, 2,4-dichlorophenoxymethyl, 2-chlorophenoxymethyl, 2,6-dichlorophenoxymethyl, 4-methoxyphenoxymethyl, 4-tert-butylphenoxymethyl, 2-methylphenoxymethyl, pyridyl, 2-pyridyl, 3-pyridyl, 4-pyridyl, triazolyl, 1,2,4-triazol-1-yl, imidazol-1-yl, isoxazolyl, 3-alkylisoxazol-5-yl, 3-isopropylisoxazol-5-yl, thiazolyl, pyrimidyl, pyrrolyl, pyrazolyl, naphthyl, 1-naphthyl, 2-naphthyl, thienyl, 2-thienyl, 3-thienyl, 2-chlorothien-3-yl, 3-bromothien-2-yl, $C_2$–$C_4$-alkenyl, ethenyl, halo-$C_2$–$C_4$-alkenyl, trans-2-chloroethenyl, 2,2-dichloroethenyl, cis-2-chloroethenyl, allyl or 2-butenyl.

Examples of suitable plant-tolerated acid addition salts are the bromides, sulfates, nitrates, phosphates, oxalates and dodecylbenzenesulfonates. The activity of the salts is due to the cation, so that in general any anion may be chosen.

Suitable plant-tolerated metal complexes are compounds of the formula VI

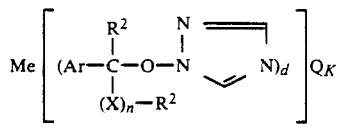

where Ar, $R^1$, $R^2$, X and n have the abovementioned meanings, Me is a metal, e.g. Cu, Zn, Sn, Mn, Fe, Co or Ni, Q is the anion of an inorganic acid, e.g. HCl, $H_2SO_4$ or $H_3PO_4$, and d and k are each 1, 2, 3 or 4. They are prepared, for example, by reacting the compounds of the formula I with a metal salt, for example copper sulfate, zinc sulfate, tin chloride or manganese sulfate.

We have furthermore found that azole compounds of the formula V are obtained if a compound of the formula II

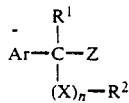

where
Ar, $R^1$, $R^2$, X and n have the abovementioned meanings and
Z is a nucleofugic leaving group, such as chlorine, bromine, methanesulfonate, benzenesulfonate or 4-toluenesulfonate, is reacted a) with an alkali metal salt of the formula III

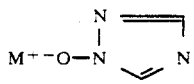

where M is sodium or potassium, in the presence or absence of a diluent, or b) with 1-hydroxy-1,2,4-triazole of the formula IV

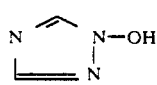

in the presence of a base of the formula V $M^+B^-$ where M is sodium or potassium and B is hydroxide, alkoxide, carbonate or hydride, in the presence or absence of a diluent, and the resulting N-hydroxytriazole derivative is, if required, converted with a metal salt into its plant-tolerated metal complexes and, if necessary, is reacted in the presence of a diluent.

It is advantageouse to react the compounds of the formula II, without a diluent or in the presence of a diluent, with about 0.5-2 equivalents of an alkali metal salt of the formula III or with about 0.5-4 equivalents of the N-hydroxytriazole of the formula IV with the addition of 0.5-4 equivalents of a base at from about 0° to 200° C., preferably from +20° to +160° C., as a homogeneous or inhomogeneous phase.

Examples of suitable diluents are methanol, ethanol, isopropanol, n-butanol, tert-butanol, diethyl ether, methyl tert-butyl ether, tetrahydrofuran, dioxane, acetone, acetonitrile, dimethylformamide, dimethyl sulfoxide, chloroform, methylene chloride or toluene. Examples of suitable bases are sodium hydroxide, hydride, methylate, ethylate, isopropylate, butylate, tert-butylate or carbonate and the corresponding potassium compounds.

The preparation of 1-hydroxy-1,2,4-triazole is described in Example 1.

Some of the compounds of Formula II are known from the literature or can be prepared by processes known from the literature.

A) For example, α-chlorosulfides of the formula II (where X is S, Z is Cl and $R^1$ is H) are obtained a) by chlorinating a sulfide with N-chlorosuccinimide (see, for example, B. L. Tuleen and T. B. Stephens, J. Org. Chem. 34 (1969), 31), for example according to the scheme

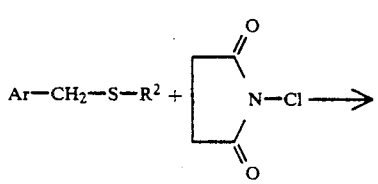

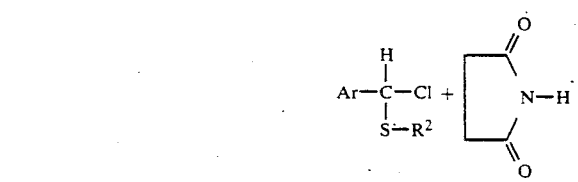

or b) by reacting an aldehyde with a thiol in the presence of hyrogen chloride (see, for example, H. Böhmer, H. Fischer and R. Frank, Liebigs Ann. Chem. 563 (1949), 54) according to the scheme

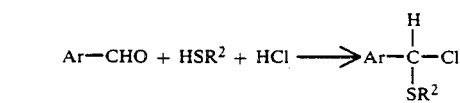

B) α-Chloroethers of the formula II (where x is 0, n is 1, Z is Cl and $R^1$ is H) are obtained, for example, a) by reacting an acetal with acetyl chloride (see, for example, D. M. Bailey, J. Med. Chem. 17 (1974), 702) according to the scheme

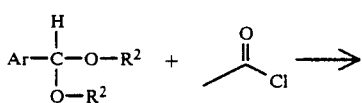

or b) by chlorinating an ether (see, for example, E. Vilsmeier, Liebigs Ann. Chem. 728 (1969), 12) according to the scheme

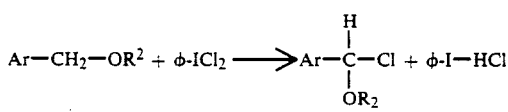

C) Compounds of the formula II where X is $CH_2$, $R^1$ is H and n is 0 or 1 are obtained either
a) by reacting an aldehyde of the formula VII

   VII with from 0.8 to 1.2 equivalents of a Grignard compound of the formula VIII

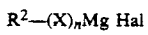   VIII or
b) by reacting an aldehyde of the formula IX

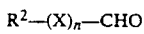   IX with from 0.8 to 1.2 equivalents of a Grignard compound of the formula X

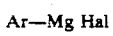   X or
c) by reducing a ketone of the formula XI

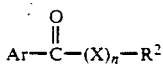   XI for example $C_1$) by the action of a complex hydride, preferably sodium borohydride, in the presence of a polar solvent, for example of an alcohol, preferably methanol or ethanol, at from 0° to 80° C., or $C_2$) by the action of hydrogen in the presence of a hydrogenation catalyst, such as platinum or Raney nickel, and in the presence of a polar solvent, such as methanol, ethanol or ethyl acetate, at from 20° to 100° C. and from 1 to 100 bar to give a compound of the formula XII

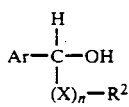   XII which is then converted in a second stage into a compound of the formula II, this being done when
a) Z is chlorine by reaction with thionyl chloride in the presence or absence of a solvent, such as methylene chloride or chloroform, at from 20° to 70° C., or when
b) Z is bromine by reaction with phosphorus tribromide in the presence or absence of a solvent, such as methylene chloride or chloroform, at from 0° to 70° C., preferably from 20° to 30° C., or when
c) Z is methanesulfonate, benzenesulfonate or 4-toluenesulfonate by reaction with the corresponding sulfonyl chlorides or sulfonic anhydrides in the presence or absence of an organic base, such as triethylamine, dimethylcyclohexylamine, diethylcyclohexylamine, pyridine or 4-N,N-dimethylaminopyridine, and in the presence or absence of a diluent, such as methyl tert-butyl ether, diethyl ether, tetrahydrofuran, methylene chloride, chloroform, pentane, hexane, cyclohexane or toluene, at from 20° to 150° C.

Compounds of the formula II where X is $CH_2$, $R^1$ is nitrile, n is 0 or 1 and Z is chlorine are obtained, for example,
a) by reacting a ketone with titanium tetrachloride in the presence of trimethylsilyl cyanide (TMS-CN) (cf. for example S. Kiyooka, R. Fujiyama and K. Kawaguchi, Chem. Lett. (1984) 1979-80) according to the scheme

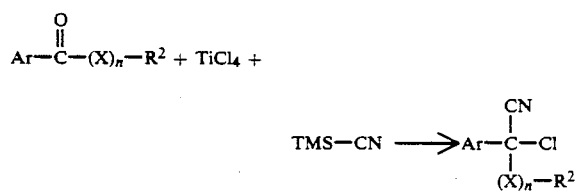

or
b) by chlorinating a nitrile with carbon tetrachloride in the presence of a 50% strength sodium hydroxide solution under phase transfer conditions (PTC) (cf. for example A. Jonczyk, A. Kwast and M. Makosza, Z. Org. Chem. 44 (1979) 1192-1194) according to the scheme

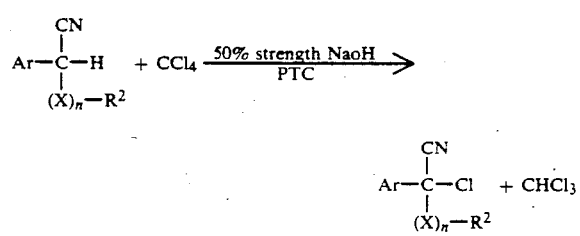

The Examples which follow describe the preparation of the novel compounds:

EXAMPLE 1 a) Preparation of 1-hydroxy-1,2,4-triazole and its potassium salt 103.5 g (1.5 mol) of 1H-1,2,4-triazole were dissolved in 1,344 g (12 mol) of 50% strength aqueous potassium hydroxide. While cooling with ice, 340 g (3 mol) of 30% strength $H_2O_2$ and, a little at a time, 555 g (3.75 mol) of phthalic anhydride were added, and the mixture was stirred for 2 hours at room temperature (from 20° to 30° C.). Thereafter, the mixture was acidified to a pH of less than 1.5 with about 35% strength sulfuric acid, the precipitate formed was filtered off under suction and the filtrate was investigated by quantitative high pressure liquid chromatography (HPLC). 65 g (51%) of a product of melting point 132° C. were obtained, which was worked up in a conventional manner.

10 g (117 mmol) of 1-hydroxy-1,2,4-triazole were dissolved in 300 ml of dimethylformamide. 13.2 g (117 mmol) of 50% strength potassium methylate and 100 ml of methanol were then added. The mixture was heated and the methanol/$H_2O$ mixture was distilled off azeotropically. A further 50 ml of methanol were added and the mixture was again distilled off azeotropically with water.

The solution of the potassium salt of 1-hydroxy-1,2,4-triazole in dimethylformamide can either be reacted directly further or the solvent is completely evaporated off to give a colorless precipitate, which is further used.

b) Preparation of di-(4-fluorophenyl)-chloromethane 15 g of anhydrous calcium chloride powder were added to 33 g of 4,4'-difluorodiphenylmethylcarbinol dissolved in 150 ml of dichloromethane, and dry hydrogen chloride was passed into the mixture at 5°–10° C. while stirring. After 2 hours, the solution was decanted off from the CaCl$_2$ and was evaporated down under reduced pressure. 34 g of di-(4-fluorophenyl)-chloromethane were obtained as a pale yellowish liquid.

c) Preparation of di-(4-fluorophenyl)-(1,2,4-triazol-1-yloxy)-methane (compound No. 1)

100 mg of potassium iodide and 2.9 g of di-(4-fluorophenyl)-chloromethane were added to 1.5 g of the potassium salt of 1-hydroxy-1,2,4-triazole in 100 ml of dimethylformamide and the mixture was stirred for 2 hours at room temperature. The solvent was evaporated off under reduced pressure, after which the residue was taken up with 50 ml of methyl tert-butyl ether and the solution was extracted twice by shaking with water. The organic phase was evaporated down to give 3.3 g of a pale yellow oil, which was chromatographed over a short silica gel column using dichloromethane. The yield was 2.0 g of a pale oil.

$^1$H-NMR (300 MHz, CDCl$_3$): 6.5 ppm (1H, s); 7.0–7.4 ppm (8H, m); 7.5 ppm (1H, s); 7.8 ppm (1H, s)

EXAMPLE 2

Preparation of 2,4-dichlorobenzylphenylthio-(1,2,4-triazol-1-yloxy)-methane (compound No. 2)

26.9 g of 2,4-dichlorobenzyl phenyl sulfide and 13.4 g of N-chlorosuccinimide in 100 ml of tetrachloromethane was stirred for 2 hours at 0° C. and the mixture was then allowed to warm up to room temperature and was stirred for a further 48 hours. Thereafter, the succinimide suspended in the mixture was filtered off and the filtrate was freed from the solvent under reduced pressure. 30.3 g of α-chloro-2,4-dichlorobenzyl phenyl sulfide remained as an oil.

4.6 g of this oil were added dropwise to a mixture of 1.5 g of the potassium salt of 1-hydroxy-1,2,4-triazole and 0.3 g of potassium iodide in 30 ml of dimethylformamide. Checking by thin layer chromatography (TLC) showed that the reaction was complete after stirring for 2 hours at room temperature. The dimethylformamide was evaporated off under reduced pressure, 50 ml of water were added to the residue and the mixture was extracted with three times 50 ml of methyl tert-butyl ether. The combined organic solutions were washed with 30 ml of water, dried over magnesium sulfate and evaporated down under reduced pressure (4.7 g of an oil) and then chromatographed over a silica gel column using diethyl ether as the mobile phase. After an initial fraction of 0.1 g, which was discarded, 1.0 g of 2,4-dichlorobenzylphenylthio-(1,2,4-traizol-1-yloxy)-methane was obtained as a pale yellow oil.

$^1$H-NMR (300 MHz, CDCl$_3$): 6.7 ppm (1H, s); 7.1–7.6 ppm (8H, m); 7.9 ppm (1H, s); 8.5 ppm (1H, s)

EXAMPLE 3 a) 2-Chloro-2,2-di-(4-fluorophenyl)-acetonitrile 4.4 g (20 mmol) of 4,4'-difluorobenzophenone were dissolved in 50 ml of CH$_2$Cl$_2$ under nitrogen gas. 2.7 ml (24 mmol) of titanium tetrachloride and 2.7 ml (20 mmol) of trimethylsilyl cyanide were then added in succession at 0° C. After 30 minutes, the mixture was allowed to warm up to room temperature and was stirred for a further 24 hours. Aqueous NaHCO$_3$ solution was added, after which the mixture was extracted with ether. The ether phase was dried over Na$_2$SO$_4$. The product was obtained in the form of a yellow oil.

Yield: 5 g

IR: 1602 cm$^{-1}$, 1508 cm$^{-1}$, 1239 cm$^{-1}$, 1163 cm$^{-1}$, 835 cm$^{-1}$ b) Cyanodi-(4-fluorophenyl)-(1,2,4-triazol-1-yloxy)-methane (compound No. 3)

1.5 g (12 mmol) of the potassium salt of N-hydroxytriazole in 20 ml of absolute dimethylformamide were initially taken under nitrogen. A solution of 3.16 g (12 mmol) of 2-chloro-2,2-di-(4-fluorophenyl)-acetonitrile in dimethylformamide was added dropwise to this solution, a slightly exothermic reaction taking place. The mixture was stirred for a further 3 hours at room temperature. The reaction solution was evaporated down, the residue was added to water and the mixture was extracted with ethyl acetate. The product was obtained from ethyl acetate in the form of a pale yellow oil, which crystallized out on stirring with diisopropyl ether.

Yield: 2.5 g

Melting point 124° C.

H-NMR: 7.15 ppm, t (4H); 7.4–7.6 ppm, m (4H); 7.72 ppm, s (1H); 7.78 ppm, s (1H)

EXAMPLE 4

1-(2,4-Dichlorophenyl)-1-(1,2,4-triazol-1-yloxy)-butane (compound No. 33)

1.2 g (10 mmol) of the potassium salt of 1-hydroxy-1,2,4-triazole were dissolved in 100 ml of dimethylformamide and the solution was added at room temperature to a solution of 4.0 g (10 mmol) of 1-bromo-1-(2,4-dichlorophenyl)-butane in 50 ml of dimethylformamide. 0.1 g of potassium iodide was added to the mixture, which was refluxed for 10 minutes. Thereafter, the solvent was removed under reduced pressure, the residue was taken up in ether and the solution was washed three times with water. After the organic phase had been dried with Na$_2$SO$_4$, the solvent was removed under reduced pressure.

The yield comprises 2.7 g (94%) of a brown oil, which was purified by column chromatography (silica gel, 1:1 ethyl acetate/cyclohexane).

TABLE

The following compounds of the formula I may be prepared similarly:

| Example No. | Ar | R$^1$ | (X)$_n$ | R$^2$ | $^1$H-NMR (ppm) mp (°C.) or IR (cm$^{-1}$) |
|---|---|---|---|---|---|
| 1 | 4-fluorophenyl | H | — | 4-fluorophenyl | v. Ex. 1 |

TABLE-continued

The following compounds of the formula I may be prepared similarly:

| Example No. | Ar | R¹ | (X)ₙ | R² | ¹H-NMR (ppm) mp (°C.) or IR (cm⁻¹) |
|---|---|---|---|---|---|
| 2 | 2,4-dichlorophenyl | H | S | phenyl | v. Ex. 2 |
| 3 | 4-fluorophenyl | CN | — | 4-fluorophenyl | v. Ex. 3 |
| 4 | 4-fluorophenyl | H | — | 2-chlorophenyl | 1510, 1235, 1003, 832, 757, 681 cm⁻¹ |
| 5 | 4-fluorophenyl | H | — | 2-fluorophenyl | 1511, 1491 1234, 1003, 760, 681 cm⁻¹ |
| 6 | 4-fluorophenyl | H | S | 2-chlorophenyl | 1509, 1451, 1233, 1226 1125, 1005, 891; 843, 766, 679 cm⁻¹ |
| 7 | 4-fluorophenyl | H | CH₂ | 2-chlorophenyl | 1606, 1511, 1436, 1228 1004, 838, 754, 681 cm⁻¹ |
| 8 | phenyl | H | — | 4-fluorophenyl | 1511, 1275, 1229, 1004, 832, 699, 681 cm⁻¹ |
| 9 | 2-fluorophenyl | H | — | phenyl | 1490, 1452, 1274, 1241, 1003, 943, 762, 698, 681 cm⁻¹ |
| 10 | 3-trifluoromethylphenyl | H | — | phenyl | 1333, 1168, 1127, 1075, 701, 682 cm⁻¹ |
| 11 | 4-chlorophenyl | H | — | 2,2-dichlorovinyl | 73-75° C. |
| 12 | 2,4-dichlorophenyl | H | S | 4-chlorophenyl | 85-87° C. |
| 13 | 2,4-dichlorophenyl | H | S | ethyl | 1589, 1497, 1472, 1275, 866, 856 cm⁻¹ |
| 14 | 4-fluorophenyl | H | — | 2-trifluoromethylbenzyl | |
| 15 | 4-fluorophenyl | H | — | 2-bromobenzyl | |
| 16 | 4-fluorophenyl | H | — | 2-methylbenzyl | |
| 17 | phenyl | H | — | 2-chlorophenyl | 1490, 1270, 1130, 1050, 748 cm⁻¹ |
| 18 | phenyl | H | CH₂ | 2-chlorophenyl | |
| 19 | phenyl | H | — | 2-(4-chlorophenyl)ethyl | |
| 20 | 4-phenylphenyl | H | — | tert.-butyl | |
| 21 | 4-phenylphenyl | H | — | n-butyl | |
| 22 | 4-phenoxyphenyl | H | — | n-hexyl | |
| 23 | 4-phenoxyphenyl | H | S | tert.-butyl | |
| 24 | 4-phenylphenyl | H | S | tert.-butyl | |
| 25 | 4-chlorophenyl | H | S | tert.-butyl | |
| 26 | 4-chlorophenyl | H | CH₂ | tert.-butyl | |
| 27 | 2-chloro-4-(4-chlorophenoxy)-phenyl | H | S | tert.-butyl | |
| 28 | 2-chloro-4-(4-chlorophenoxy)-phenyl | H | S | ethyl | |
| 29 | 2-chloro-4-(4-chlorophenoxy)-phenyl | H | S | methyl | |
| 30 | 2-chloro-4-(4-chlorophenoxy)-phenyl | H | S | 2-methylpropyl | |
| 31 | 4-chlorophenyl | H | — | 2-cyclopropyl-ethyl-(2) | |
| 32 | 4-methylphenyl | H | — | 2-cyclopropyl-ethyl-(2) | |
| 33 | 2,4-dichlorophenyl | H | — | n-propyl | 1510, 1470, 1380, 1273, 1240, 1100, 965, 680 cm⁻¹ |
| 34 | 2,4-dichlorophenyl | H | — | n-hexyl | |
| 35 | 2,4-dichlorophenyl | H | S | methyl | |
| 36 | 1-naphthyl | H | S | n-propyl | |
| 37 | 2-naphthyl | H | S | n-butyl | |
| 38 | 2,4-dichlorophenyl | H | S | cyclohexyl | |
| 39 | 2-chloro-4-(4-chlorophenoxy)-phenyl | H | — | ethyl | |
| 40 | 2-chloro-4-(4-chlorophenoxy)-phenyl | H | — | n-butyl | |
| 41 | 4-(4-chlorophenoxy)-phenyl | H | — | n-propyl | |
| 42 | 2-thienyl | H | — | 2-chlorophenyl | |
| 43 | 2-thienyl | H | S | 4-chlorophenyl | |
| 44 | 2-thienyl | H | CH₂ | 2-bromophenyl | |
| 45 | 3-thienyl | H | — | 2-trifluoromethylphenyl | |
| 46 | 3-thienyl | H | S | 2-chlorophenyl | |
| 47 | 2-pyridyl | H | — | 2-chlorophenyl | |

TABLE-continued

The following compounds of the formula I may be prepared similarly:

| Example No. | Ar | R¹ | (X)ₙ | R² | ¹H-NMR (ppm) mp (°C.) or IR (cm⁻¹) |
|---|---|---|---|---|---|
| 48 | 2-pyridyl | H | — | 4-chlorophenyl | |
| 49 | 4-chloro-2-pyridyl | H | — | 2-chlorophenyl | |
| 50 | 4-chloro-2-pyridyl | H | — | 4-fluorophenyl | |
| 51 | 4-chloro-2-pyridyl | H | — | n-propyl | |
| 52 | 4-chloro-2-pyridyl | H | — | 2-methylpropyl | |
| 53 | 4-chloro-2-pyridyl | H | S | n-butyl | |
| 54 | 4-methoximino-phenyl | H | — | n-butyl | |
| 55 | 4-ethoximinophenyl | H | S | tert.-butyl | |
| 56 | 4-isopropoximino | H | S | tert.-butyl | |
| 57 | 4-methoximino | H | S | ethyl | |
| 58 | 4-methoximino | H | S | n-hexyl | |
| 59 | 4-methoximino | H | S | 2-chlorophenyl | |
| 60 | 4-ethoximino | H | — | phenyl | |
| 61 | 4-n-butoximino | H | S | n-butyl | |
| 62 | 4-methoximino | H | CH₂ | phenyl | |
| 63 | 4-methoximino | H | CH₂ | 2-chlorophenyl | |
| 64 | 4-methoximino | H | CH₂ | tert.-butyl | |
| 65 | phenyl | H | CH₂ | 2,4-dichlorophenyl | |
| 66 | 4-fluorophenyl | H | CH₂ | 4-chlorobenzyl | |
| 67 | 2,4-dichlorophenyl | H | CH₂ | n-propyl | |
| 68 | phenyl | H | CH₂ | 3-phenylpropyl-(1) | |
| 69 | phenyl | H | O | phenyl | |
| 70 | phenyl | H | O | 2-chlorophenyl | |
| 71 | phenyl | H | O | benzyl | |
| 72 | phenyl | H | O | tert.-butyl | |
| 73 | 4-fluorophenyl | H | O | tert.-butyl | |
| 74 | 4-chlorophenyl | H | O | tert.-butyl | |
| 75 | 2,4-dichlorophenyl | H | O | n-butyl | |
| 76 | 2,4-dichlorophenyl | H | O | 2-methylpropyl | |
| 77 | 2,4-dichlorophenyl | H | O | tert.-butyl | |
| 78 | 4-fluorophenyl | H | O | 2-chlorophenyl | |
| 79 | 4-fluorophenyl | H | O | 2,6-dichlorophenyl | |
| 80 | 4-fluorophenyl | H | O | 2,4-dichlorophenyl | |
| 81 | 4-phenylphenyl | H | O | n-butyl | |
| 82 | 4-tert.-butyl-phenyl | H | S | tert.-butyl | |
| 83 | 4-tert.-butylphenyl | H | S | n-butyl | |
| 84 | phenyl | H | — | 4-tert.-butylphenyl | |
| 85 | 2,4-dichlorophenyl | H | — | 4-methoxyphenyl | |
| 86 | 4-fluorophenyl | H | — | 2-methoxyphenyl | |
| 87 | 4-fluorophenyl | H | — | 2-phenoxyethyl | |
| 88 | 4-fluorophenyl | H | — | 4-phenoxybutyl | |
| 89 | phenyl | H | — | 3-phenoxypropyl | |
| 90 | phenyl | H | — | 2-(2-chlorophenoxy)ethyl-(1)- | |
| 91 | 4-fluorophenyl | H | — | 3-(2-fluorophenoxy-)propyl-(1)- | |
| 92 | 4-fluorophenyl | H | — | 2-pyridyl | |
| 93 | phenyl | H | — | 4-pyridyl | |
| 94 | phenyl | H | — | 2-thienyl | |
| 95 | 4-fluorophenyl | H | — | 3-thienyl | |
| 96 | 4-fluorophenyl | H | — | 4-chloro-2-pyridyl | |
| 97 | 4-fluorophenyl | H | — | 3-chloro-4-pyridyl | |
| 98 | 4-fluorophenyl | H | S | 2-pyridyl | |
| 99 | 4-trifluoromethylphenyl | H | S | 2-bromophenyl | |
| 100 | 2,4-dichlorophenyl | H | S | 3-propynyl-1 | |
| 101 | 2,4-dichlorophenyl | H | — | ethynyl | |
| 102 | 2,4-dichlorophenyl | H | — | vinyl | |
| 103 | 4-phenylphenyl | H | — | propenyl | |
| 104 | 4-phenylphenyl | H | S | 2,3,3-trichloropropenyl | |
| 105 | phenyl | CN | — | 4-fluorophenyl | |
| 106 | phenyl | CN | — | 2-chlorophenyl | |
| 107 | phenyl | CN | — | 2,4-dichlorophenyl | |
| 108 | 4-fluorophenyl | CN | — | 2-chlorophenyl | 1509, 1238, 985, 760, 680 |
| 109 | 4-fluorophenyl | CN | — | 4-chlorophenyl | |
| 110 | 4-fluorophenyl | CN | — | 2-chlorobenzyl | |
| 111 | 4-fluorophenyl | CN | — | n-butyl | |
| 112 | 4-fluorophenyl | CN | — | tert.-butyl | |
| 113 | 2,4-dichlorophenyl | CN | — | ethyl | |
| 114 | 2,4-dichlorophenyl | CN | — | n-butyl | |
| 115 | 2,4-dichlorophenyl | CN | — | 2-methylpropyl | |
| 116 | 4-chlorophenyl | CN | — | 2-cyclopropylethyl-(2) | |
| 117 | 4-fluorophenyl | CN | — | 2-cyclopropylethyl-(2) | |
| 118 | 4-chlorophenyl | CN | — | tert.-butyl | |
| 119 | 2,4-dichlorophenyl | CN | — | n-hexyl | |
| 120 | 4-fluorophenyl | CN | — | 2-trifluoromethylbenzyl | |
| 121 | 2-chloro-4-(4-chlorophenoxy)-phenyl | CN | — | ethyl | |
| 122 | 2-chloro-4-(4-chlorophenoxy)-phenyl | CN | — | n-butyl | |

TABLE-continued

The following compounds of the formula I may be prepared similarly:

| Example No. | Ar | R¹ | (X)ₙ | R² | ¹H-NMR (ppm) mp (°C.) or IR (cm⁻¹) |
|---|---|---|---|---|---|
| 123 | 4-fluorophenyl | CN | — | 2-fluorophenyl | 1510, 1491, 1454, 1239, 996, 837, 763, 680, cm⁻¹ |
| 124 | 4-chlorophenyl | CN | — | 2-chlorophenyl | 1492, 1274, 1095, 995, 824, 760, 680 cm⁻¹ |
| 125 | phenyl | H | — | phenyl | |
| 126 | 4-chlorophenyl | H | — | 2-chlorophenyl | |
| 127 | 4-chlorophenyl | H | — | phenyl | 1493, 1275, 1239, 1088, 940, 680 cm⁻¹ |
| 128 | 4-chlorophenyl | H | — | 4-chlorophenyl | 1493, 1275, 1241, 1092, 820, 805, 679 cm⁻¹ |
| 129 | 4-chlorophenyl | H | — | n-propyl | 1490, 1275, 1240, 1090, 945, 870, 680 cm⁻¹ |
| 130 | 4-fluorophenyl | H | — | n-propyl | 1510, 1275, 1225, 1005, 835, 680 cm⁻¹ |
| 131 | 4-chlorophenyl | H | — | 4-methylbutyl | 1492, 1270, 1090, 940, 825, |
| 132 | 4-chlorophenyl | H | — | 3-isopropylisoxazol-5-yl | |
| 133 | 4-fluorophenyl | H | — | 3-isopropylisoxazol-5-yl | 3.07 (sept,1H), 6.2 (s,1H), 6.5 (s,1H), 7.68 (s,1H), 7.75 (s,1H) ppm) |
| 134 | 2,4-dichlorophenyl | H | — | 3-pyridyl | |
| 135 | 4-fluorophenyl | H | — | 3-pyridyl | |
| 136 | 4-fluorophenyl | H | — | 1,2,4-triazol-1-yl | |
| 137 | 4-methoximinophenyl | H | — | 4-fluorophenyl | |
| 138 | phenyl | CN | — | 2-(4-chlorophenyl)ethyl | 7.1 (d,2H), 7.26 (d,2H), 7.62 (s,1H), 7.68 (s,1H) ppm |
| 139 | 4-fluorophenyl | CN | — | 2-(4-chlorophenyl)ethyl | 2.45-3.08(m,4H); 7.65(s,1H); 7.8(s,1H) |
| 140 | 4-chlorophenyl | CN | — | " | |
| 141 | 2,4-dichlorophenyl | CN | — | " | 2.65-3.02(m,4H); 7.69(s,1H); 8.13(s,1H) |
| 142 | phenyl | CN | — | 2-(4-fluorophenyl)ethyl | 2.5-3.04(m,4H); 7.66(s,1H); 7.74(s,1H) |
| 143 | 4-fluorophenyl | CN | — | " | 2.5-3.06(m,4H); 7.65(s,1H); 7.85(s,1H) |
| 144 | 4-chlorophenyl | CN | — | " | 2.48-3.04(m,4H); 7.66(s,1H); 7.86(s,1H) |
| 145 | 2,4-dichlorophenyl | CN | — | " | 2.65-3.05(m,4H); 7.68(s,1H); 8.14(s,1H) |
| 146 | phenyl | CN | — | 2-(phenyl)ethyl | 2.5-3.1(m,4H); 7.65(s,1H); 7.82(s,1H) |
| 147 | 4-fluorophenyl | CN | — | " | 2.66-3.08(m,4H); 7.7(s,1H); 8.15(s,1H) |
| 148 | 4-chlorophenyl | CN | — | " | |
| 149 | 2,4-dichlorophenyl | CN | — | " | 2.66-3.08(m,4H); 7.7(s,1H); 8.15(s,1H) |
| 150 | phenyl | CN | — | 2(2,4-dichlorophenyl)ethyl | |
| 151 | 4-fluorophenyl | CN | — | " | |
| 152 | 4-chlorophenyl | CN | — | " | |
| 153 | 2,4-dichlorophenyl | CN | — | " | |
| 154 | 4-fluorophenyl | H | — | 2,4-dichlorophenyl | 6.77(s,1H); 7.62(s,1H); 7.77(s,1H) |
| 155 | 4-fluorophenyl | H | — | 3-(p-tert.-butylphenyl)-isoxazol-5-yl | 1.35(s,9H); 6.6(s,1H); 6.65(s,1H); 7.72(s,1H); 7.78(s,1H) |
| 156 | 4-fluorophenyl | H | — | 3-tert.-butylisoxazol-5-yl | 1.32(s,9H); |

TABLE-continued

The following compounds of the formula I may be prepared similarly:

| Example No. | Ar | R¹ | (X)$_n$ | R² | ¹H-NMR (ppm) mp (°C.) or IR (cm$^{-1}$) |
|---|---|---|---|---|---|
| | | | | | 6.25(s,1H); 6.54(s,1H); 7.66(s,1H); 7.76(s,1H) |
| 157 | 4-fluorophenyl | H | — | 3-n-propylisoxazol-5-yl | 6.2(s,1H); 6.55(s,1H); 7.72(s,1H); 7.78(s,1H) |
| 158 | 4-fluorophenyl | H | — | 3-cyclopentylisoxazol-5-yl | 6.16(s,1H); 6.52(s,1H); 7.68(s,1H); 7.77(s,1H) |
| 159 | 4-fluorophenyl | H | — | 3-sec.-butylisoxazol-5-yl | 6.17(s,1H); 6.53(s,1H); 7.66(s,1H); 7.77(s,1H) |

Generally speaking, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawn, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi. It is possible to treat either the fungi themselves, or the plants, seeds, materials or the soil to be protected against fungus attack.

The growth-regulating salicylic acid derivatives of the formula I may exercise a variety of influences on practically all plant development stages, and are therefore used as growth regulators. The diversity of action of growth regulators depends especially on
a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The reduction in vegetative growth is also important in fruit and other trees, thus saving on pruning costs.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The active ingredients of the formula I may raise the yield by influencing plant metabolism or by promoting or inhibiting vegetative and/or generative plant growth.

C. It is also possible with the compounds of the formula I to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a dressing), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.005 to 0.5, g per kg of seed are generally required. For foliage and soil treatment, amounts of from 0.01 to 10, preferably from 0.05 to 1, kg/ha are generally considered sufficient.

The agents can be employed in the form of conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylenes, toluene, benzene), chlorinated aromatics (e.g., chlorobenzenes), paraffins (e.g., crude oil fractions), alcohols (e.g., methanol, butanol), amines (e.g., ethanolamine) N,N-dimethylformamide, and water; solid carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates); and dispersants such as lignin, sulfite waste liquors and methylcellulose.

The fungicidal and growth-regulating agents generally contain from 0.1 to 95, and preferably from 0.5 to 90, wt % of active ingredient.

When the active ingredients are used as fungicides, the application rates depend on the desired effect, and range from 0.02 to 3 kg/ha. The novel compounds may also be used for protecting materials (timber), e.g., against Paecilomyces variotii.

The agents, or the ready-to-use formulations prepared therefrom, such as solutions, emulsions, suspensions, powders, dusts, pastes or granules, are applied in known manner, for example by spraying, atomizing, dusting, broadcasting, treating seed, or by watering.

Examples of formulations are given below.

I. A solution of 90 parts by weight of compound no. 1 and 10 parts by weight of N-methyl-α-pyrrolidone, which is suitable for application in the form of very fine drops.

II. A mixture of 20 parts by weight of compound no. 3, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 4, 40 parts by weight of cyclohexanone, 30 parts by weight of isobutanol, and 20 parts by weight of the adduct of 40 moles of ethylene oxide and 1 mole of castor oil. An aqueous dispersion is obtained by pouring the solution into water and finely distributing it therein.

IV. An aqueous dispersion of 20 parts by weight of compound no. 5, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. An aqueous dispersion is obtained by pouring the solution into water and finely distributing it therein.

V. A hammer-milled mixture of 80 parts by weight of compound no. 6, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 7 and 97 parts by weight of particulate kaolin. The dust contains 3 wt % of the active ingredient.

VII. An intimate mixture of 30 parts by weight of compound no. 9, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 17, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 33, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the fungicidal agents according to the invention may also be present together with other active ingredients, for example herbicides, insecticides, growth regulators, and fungicides, and may furthermore be mixed and applied together with fertilizers. Admixture with other fungicides often results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloranilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl-1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate, methyl DL-N-(2,6-dimethylphenyl)-N-(2'-methoxyacetyl)-alanate,
N-(2,6-dimethylphenyl)-N-chloroacetyl-DL-2-aminobutyrolactone, methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole, 2,4-difluoro-α-(1H-1,2,4-triazol-1-ylmethyl)-benzhydryl alcohol, N-(3-chloro-2,6-dinitro-4-trifluoromethylphenyl)-5-trifluoromethyl-3-chloro-2-aminopyridine, and 1-((bis-(4-fluorophenyl)-methylsilyl)-methyl)-1H-1,2,4-triazole.

USE EXAMPLES

The active ingredient 1-bis-(4-fluorophenyl)-methyl-1H-1,2,4-triazole (A) disclosed in EP 165,777 was used for comparison purposes.

USE EXAMPLE 1

Action on Wheat Mildew

Leaves of pot-grown wheat seedlings of the "Kanzler" variety were sprayed with aqueous liquors containing (dry basis) 80% of active ingredient and 20% of emulsifier, and dusted, 24 hours after the sprayed-on layer had dried, with spores of wheat mildew (Erysiphe graminis var. tritici). The plants were then set up in the greenhouse at from 20° to 22° C. and a relative humidity of from 75 to 80%. The extent of mildew spread was assessed after 7 days.

The results show that active ingredients 1, 3, 4, 5, 6, 7, 9, 17, 33, 108, 123, 124, 127, 128 and 129, applied as 0.006 wt % spray liquors, have a better fungicidal action (95%) than prior art comparative agent A (75%).

USE EXAMPLE 2

Action on Wheat Brown Rust

Leaves of pot-grown wheat seedlings of the "Kanzler" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 1, 4, 7, 127 and 128, applied as 0.025% spray liquors, have a better fungicidal action (95%) than prior art comparative agent A (30%).

We claim:

1. A compound of the formula I

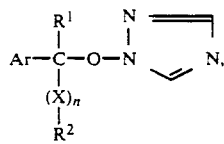

where

Ar is phenyl which is unsubstituted or monosubstituted or polysubstituted by halogen, $C_1$–$C_4$-alkoxy, $C_1$–$C_4$-alkyl, trifluoromethyl, $C_1$–$C_4$-alkoximino or by unsubstituted or halogen- or trifluoromethyl-substituted phenyl or phenoxy, or is pyridyl which is unsubstituted or substituted by the same radicals, thienyl which is unsubstituted or substituted by the same radicals or naphthyl which is unsubstituted or substituted by the same radicals, $R^1$ is hydrogen, or, where n is 0, is additionally CN, $R^2$ is phenyl or naphthyl, each of which is unsubstituted or monosubstituted or polysubstituted by halogen, $C_1$–$C_4$-alkyl, $C_1$–$C_4$-alkoxy, trifluoromethyl or $C_1$–$C_4$-alkoximino, or is hetaryl which is unsubstituted or substituted by the same radicals, or is unsubstituted or $C_1$–$C_4$-alkyl-substituted $C_3$–$C_8$-cycloalkyl or is straight-chain or branched $C_1$–$C_6$-alkyl which is unsubstituted or monosubstituted or polysubstituted by halogen, $C_3$–$C_6$-cycloalkyl, phenyl, halophenyl, $C_1$–$C_4$-alkylphenyl, trifluoromethylphenyl, phenoxy, halophenoxy, lower alkoxyphenoxy or lower alkylphenoxy, or is $C_2$–$C_6$-alkenyl which is unsubstituted or substituted by the same radicals, or is $C_2$–$C_6$-alkynyl which is unsubstituted or substituted by the same radicals, wherein hetaryl is selected from the group consisting of 2-, 3-, or 4-pyridyl; 2- or 3-thienyl; 1,2,4-triazol-1-yl; imidazol-1-yl; 3-lower alkylisoxazol-5-yl; 3-cyclopentylisoxazol-5-yl; 3-(p-tert.-butylphenyl)isoxazol-5-yl; pyrimidyl; thiazolyl; pyrrolyl; and pyrazolyl;

X is $CH_2$, O or S and n is 0 or 1, or a plant-tolerated acid addition salt or metal complex thereof.

2. A fungicidal composition containing an inert solid or liquid carrier and a fungicidally effective amount of a compound of the formula I

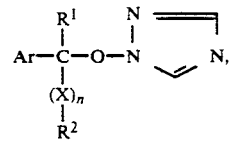

where

Ar is phenyl which is unsubstituted or monosubstituted or polysubstituted by halogen, $C_1$–$C_4$-alkoxy, $C_1$–$C_4$-alkyl, trifluoromethyl, $C_1$–$C_4$-alkoximino or by unsubstituted or halogen- or trifluoromethyl-substituted phenyl or phenoxy, or is pyridyl which is unsubstituted or substituted by the same radicals, thienyl which is unsubstituted or substituted by the same radicals or naphthyl which is unsubstituted or substituted by the same radicals, $R^1$ is hydrogen, or, where n is 0, is additionally CN, $R^2$ is phenyl or naphthyl, each of which is unsubstituted or monosubstituted or polysubstituted by halogen, $C_1$–$C_4$-alkyl, $C_1$–$C_4$-alkoxy, trifluoromethyl or $C_1$–$C_4$-alkoximino, or is hetaryl which is unsubstituted or substituted by the same radicals, or is unsubstituted or $C_1$–$C_4$-alkyl-substituted $C_3$–$C_8$-cycloalkyl or is straight-chain or branched $C_1$–$C_6$-alkyl which is unsubstituted or monosubstituted or polysubstituted by halogen, $C_3$–$C_6$-cycloalkyl, phenyl, halophenyl, $C_1$–$C_4$-alkylphenyl, trifluoromethylphenyl, phenoxy, halophenoxy, lower alkoxyphenoxy or lower alkylphenoxy, or is $C_2$–$C_6$-alkenyl which is unsubstituted or substituted by the same radicals, or is $C_2$–$C_6$-alkynyl which is unsubstituted or substituted by the same radicals, wherein hetaryl is selected from the group consisting of 2-, 3-, or 4-pyridyl; 2- or 3-thienyl; 1,2,4-triazol-1-yl; imidazol-1-yl; 3-lower alkylisoxazol-5-yl; 3-cyclopentylisoxazol-5-yl; 3-(p-tert.-butylphenyl)isoxazol-5-yl; pyrimidyl; thiazolyl; pyrrolyl; and pyrazolyl;

X is $CH_2$, O or S and n is 0 or 1, or a plant-tolerated acid addition salt or metal complex thereof.

3. A process for combating fungi, wherein a fungicidally effective amount of a compound of the formula I

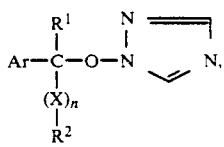

where

Ar is phenyl which is unsubstituted or monosubstituted or polysubstituted by halogen, $C_1$–$C_4$-alkoxy, $C_1$–$C_4$-alkyl, trifluoromethyl, $C_1$–$C_4$-alkoximino or by unsubstituted or halogen- or trifluoromethyl-substituted phenyl or phenoxy, or is pyridyl which is unsubstituted or substituted by the same radicals, thienyl which is unsubstituted or substituted by the same radicals or naphthyl which is unsubstituted or substituted by the same radicals, $R^1$ is hydrogen, or, where n is 0, is additionally CN, $R^2$ is phenyl or naphthyl, each of which is unsubstituted or monosubstituted or polysubstituted by halogen, $C_1$–$C_4$-alkyl, $C_1$–$C_4$-alkoxy, trifluoromethyl or $C_1$–$C_4$-alkoximino, or is hetaryl which is unsubstituted or substituted by the same radicals, or is unsubstituted or $C_1$–$C_4$-alkyl-substituted $C_3$–$C_8$-cycloalkyl or is straight-chain or branched $C_1$–$C_6$-alkyl which is unsubstituted or monosubstituted or polysubstituted by halogen, $C_3$–$C_6$-cycloalkyl, phenyl, halophenyl, $C_1$–$C_4$-alkylphenyl, trifluoromethylphenyl, phenoxy, halophenoxy, lower alkoxyphenoxy or lower alkylphenoxy, or is $C_2$–$C_6$-alkenyl which is unsubstituted or substituted by the same radicals, or is $C_2$–$C_6$-alkynyl which is unsubstituted or substituted by the same radicals, wherein hetaryl is selected from the group consisting of 2-, 3-, or 4-pyridyl; 2- or 3-thienyl; 1,2,4-triazol-1-yl; imidazol-1-yl; 3-lower alkylisoxazol-5-yl; 3-cyclopentylisoxazol-5-yl; 3-(p-tert.-butylphenyl)isoxazol-5-yl; pyrimidyl; thiazolyl; pyrrolyl; and pyrazolyl;

X is $CH_2$, O or S and n is 0 or 1, or a plant-tolerated acid addition salt or metal complex thereof, is allowed to act on the fungi, or the plant materials, plants, seed or the soil threatened by fungus attack.

4. A compound of the formula I as set forth in claim 1, where Ar is 4-fluorophenyl, $R^1$ is H, n is 0 and $R^2$ is 4-fluorophenyl.

5. A compound of the formula I as set forth in claim 1, where Ar is 2,4-dichlorophenyl, $R^1$ is H, n is 0 and $R^2$ is n-propyl.

* * * * *